United States Patent [19]

Brown

[11] 4,117,129

[45] Sep. 26, 1978

[54] INDOLOBENZOXAZEPINES AS CNS DEPRESSANTS

[75] Inventor: Richard E. Brown, Hanover, N.J.

[73] Assignee: Warner-Lambert Company, Morris Plains, N.J.

[21] Appl. No.: 831,629

[22] Filed: Sep. 8, 1977

Related U.S. Application Data

[60] Continuation-in-part of Ser. No. 734,791, Oct. 22, 1976, Pat. No. 4,066,660, which is a division of Ser. No. 620,734, Oct. 8, 1975, Pat. No. 4,013,641.

[51] Int. Cl.$^2$ .................. A61K 27/00; A61K 31/40; A61K 31/54; A61K 31/495
[52] U.S. Cl. .................. 424/248.57; 424/246; 424/250; 424/267; 424/274
[58] Field of Search ............... 424/246, 250, 267, 274, 424/248.57

Primary Examiner—Stanley J. Friedman
Attorney, Agent, or Firm—Albert H. Graddis; Frank S. Chow; George M. Yahwak

[57] ABSTRACT

This invention relates to substituted indolobenzoxazepines which act as central nervous system depressants and as such are useful as tranquillizers.

14 Claims, No Drawings

INDOLOBENZOXAZEPINES AS CNS DEPRESSANTS

This application is a continuation-in-part application of U.S. Ser. No. 734,791, filed Oct. 22, 1976, which is now U.S. Pat. No. 4,066,660, and which in turn is a divisional application of U.S. Ser. No. 620,734, filed Oct. 8, 1975 which is now U.S. Pat. No. 4,013,641.

This invention relates to substituted indolobenzoxazepines of the following general formula:

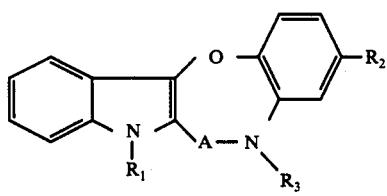
I

In this formula, $R_1$ may be hydrogen, lower alkyl of 1 to 6 carbon atoms or an aralkyl group of 1 to 6 carbon atoms in the chain; $R_2$ may be hydrogen, a halogen atom such as fluorine or chlorine, lower alkyl of 1 to 6 carbon atoms or a trifluoromethyl group. "A" may be a methylene group or a carbonyl group. $R_3$ may be hydrogen, lower alkyl of 1 to 6 carbon atoms, an aralkyl group of 1 to 6 carbon atoms in the chain, or an ω-aminoalkyl group of the formula

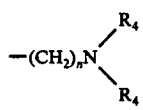

in which n may be 2 to 4 and $R_4$ may be hydrogen, lower alkyl of 1 to 6 carbon atoms or, taken together with the N atom may form a heterocyclic ring of the formula

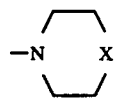

wherein X may be oxygen, sulfur, —$CH_2CH_2$—, a bond connecting the adjacent carbon atoms or CH—$R_3$ or N—$R_5$ wherein $R_5$ may be hydrogen or lower alkyl of 1 to 6 carbon atoms.

The products of this invention may be prepared according to the following reaction sequence starting with an ester of indoxylic acid, II:

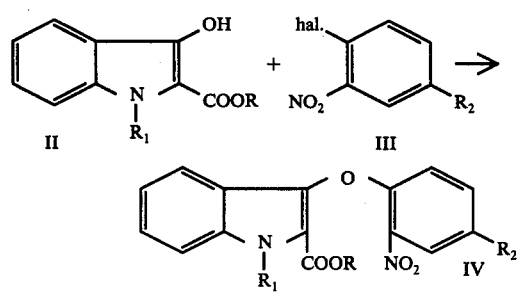

In structure II, R is a lower alkyl group of 1 to 6 carbon atoms and $R_1$ is as defined for I. These starting materials are known and were prepared according to methods described in the literature.

In the first step, the indoxylate ester is alkylated with an appropriately substituted o-halonitrobenzene of structure III to give an intermediate according to structure IV. In structure III, hal. refers to halogen and may be fluorine, chlorine, bromine or iodine. $R_2$ is as defined for structure I. This alkylation is carried out in a solvent such as a lower alcohol, THF, or, preferably, DMF in the presence of a weak base such as potassium carbonate.

In the second step, the nitro group of intermediate IV is reduced to give an amino group, as shown in structure V:

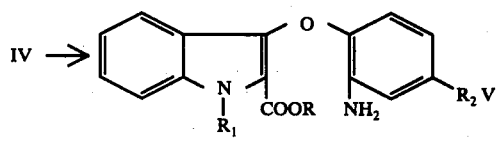

This reduction can be done catalytically in a solvent such as ethanol and using a catalyst such as platinum oxide, palladium on carbon or Raney Nickel, or it may be done chemically in a solvent such as ethanol using a metal such as iron filings or zinc dust in the presence of an acid such as hydrochloric or acetic.

In the third step, the amino ester of structure V is hydrolyzed to give the amino acid of structure VI:

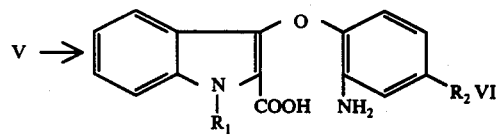

This hydrolysis is best carried out in an aqueous-alcoholic solvent system using an alkali metal hydroxide such as sodium or potassium hydroxide.

Alternatively, the order of sequence of the reduction and hydrolysis steps may be reversed so that intermediate IV is first hydrolyzed to afford a nitro acid of structure VII which is subsequently reduced to give VI.

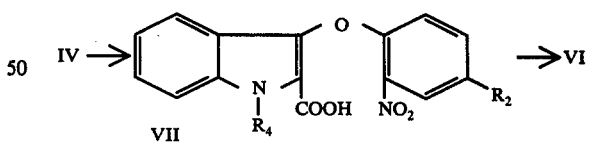

In the fourth step, ring closure of aminoacid VI to lactam VIII is carried out in a solvent such as ethanol or, preferably, THF, using an amide forming reagent such as dicyclohexylcarbodiimide, or, preferably, ethyl 1,2-dihydro-2-ethoxy-1-quinoline carboxylate.

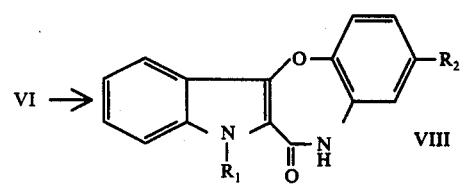

In the fifth step, lactam VIII is alkylated with an appropriately substituted halide, $R_3$ hal., to give a product of structure IX. The halides for this alkylation are selected from the group consisting of halides of lower alkanes of 1 to 6 carbon atoms, aralkyl halides containing 1 to 6 carbon atoms in the chain, or ω-aminoalkyl halides of the formula:

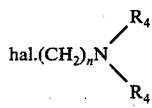

in which hal., $n$ and $R_4$ are as previously defined.

The alkylation is best carried out in polar aprotic solvents such as DMF or DMSO using a strong base such as sodium or potassium hydride or amide as the catalyst.

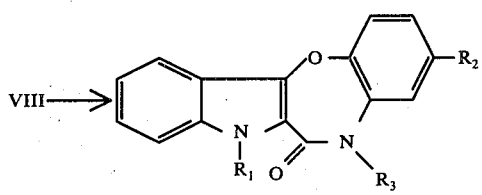

IX

In the final step, the compound of structure IX is reduced to afford a compound according to structure X. This reduction is best carried out with a complete hydride reagent such as lithium aluminum hydride in a solvent such as ether or THF.

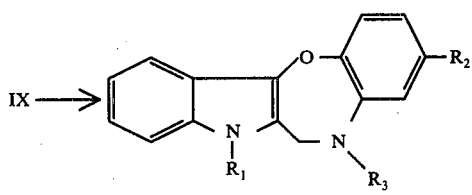

X

In order to prepare products in which $R_1$ is other than hydrogen, two methods may be used. In the first method, an $R_1$ substituted indoxylic ester is employed in step 1. Such starting materials may be synthesized according to the procedure exemplified in example 14. In the second method, an alkylation step may be carried out on structure IV wherein $R_1 = H$. This alkylation is best carried out using a polar aprotic solvent such as THF, DMF or DMSO and a strong base such as sodium hydride or potassium amide as solvent. Among the alkylating agents which may be used are halides of alkanes of 1 to 6 carbon atoms, or aralkyl halides of 1 to 6 carbon atoms in the chain.

In another aspect of the invention, there is provided a pharmaceutical composition comprising a compound of formula I as has been defined or a pharmaceutically acceptable salt thereof together with a pharmaceutically acceptable carrier.

The pharmaceutically acceptable salts of the free compounds of general formula I may be prepared by conventional reactions with equivalent amounts of inorganic or organic acid solutions. As exemplary of pharmaceutically acceptable salts there are the salts of hydrochloric, hydrobromic, sulfuric, benzenesulphonic, acetic, oxalic, malic, and citric acids.

The compounds of general formula I, as well as their pharmaceutically acceptable inorganic and organic acid salts, may be administered enterally or parenterally in admixture with a liquid or solid pharmaceutical diluent or carrier. As injection medium it is preferred to use water which contains the conventional pharmaceutical adjuvants for injection solutions such as stabilizing agents, solubilizing agents and buffers, for example, ethanol, complex-forming agents such as ethylene diamene tetraacetic acid, tartrate, and citrate buffers and highly molecular weight polymers such as polyethylene oxide for viscosity regulation. Examples of carrier materials include starch, lactose, mannitol, methylcellulose, talc, highly dispersed silicic acids, high molecular weight fatty acids such as stearic acid, and high molecular weight polymers such as polyethylene glycols. Oral forms of administration may, of course, contain flavoring, sweetening, preserving, suspending, thickening, or emulsifying agents.

A particular aspect of the formula composition comprises a compound of formula I in an effective unit dose form. By "effective unit dose" is meant a predetermined amount sufficient to be effective to bring about the desired central nervous system depressant reaction.

In yet a further aspect of the invention, there is provided a method of depressing the central nervous system in mammals, including man, which comprises the administration of an effective depressant amount of a compound of general formula I or a pharmaceutically acceptable salt thereof.

The dosage of the compounds of formula I or their pharmaceutically acceptable salts depends, of course, on the nature and severity of the excitability to be countered, as well as the path of administration. When tested in accordance with recognized protocols to determine activity in blocking conditioned avoidance in rats, the compound of structure XI, for example, was active at a dose of 10 mg/kg and the compound of structure XII was a depressant of motor activity in rats at 31 mg/kg. The compounds and their pharmaceutically acceptable salts were found to be active as CNS depressants in mammals when administered orally, parenterally, or intravenously throughout a dose range of 1.0 – 50.0 mg/kg of mammalian body weight.

It is believed that one of ordinary skill in the art, can, using the preceding description, utilize the present invention to its fullest extent. The following specific embodiments, are, therefore, to be simply construed as merely illustrative and not to limit the remainder of the specification and claims in any way whatsoever.

EXAMPLE 1

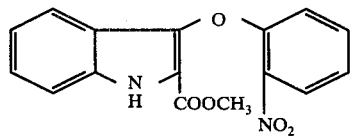

Methyl-3-[o-nitrophenoxy]-indole-2-carboxylate.

A mixture of 5.73g (0.03 mole) of methyl indoxylate, 4.23g (0.03 mole) of o-fluoronitrobenzene, 4.14g (0.03 mole) of potassium carbonate and 50ml of DMF was heated with stirring for 6 hours on the steam bath. The mixture was cooled, poured into water and filtered to give 6.7g of crude product. Recrystallization from acetonitrile gave analytical material, mp. 201°–2°.

Anal. Calcd. for $C_{16}H_{12}N_2O_5$: C, 61.54; H, 3.87; N, 8.97. Found: C, 61.39; H, 3.92; N, 8.45.

EXAMPLE 2

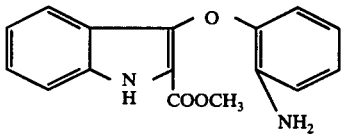

Methyl-3-[o-aminophenoxy]-indole-2-carboxylate

A mixture of 3.12g of methyl-3-[o-nitrophenoxy]-indole-2-carboxylate, 10g of 40 mesh iron filings, 5ml of 5% aqueous acetic acid and 300ml of ethanol was refluxed with stirring for 3 hours. The mixture was filtered and concentrated to a solid. Recrystallization from ethanol gave analytical material, mp. 183°–4°.

Anal. Calcd. for $C_{16}H_{14}N_2O_3$: C, 68.08; H, 5.00; N, 9.92. Found: C, 67.88; H, 5.19; N, 9.93.

EXAMPLE 3

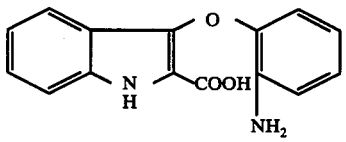

3-[o-aminophenoxy]-indole-2-carboxylic acid 1.6g of methyl-3-[o-aminophenoxy]-indole-2-carboxylate was dissolved in 10ml each of ethanol and water and refluxed for 10 min. The clear solution was acidified with acetic acid. The white precipitate was filtered and recrystallized from acetonitrile to give analytical material, mp. 217°–18°.

Anal. Calcd. for $C_{15}H_{12}N_2O_3$: C, 67.15; H, 4.51; N, 10.44. Found: C, 66.94; H, 4.59; N, 10.47.

EXAMPLE 4

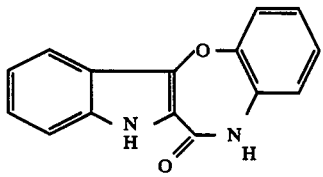

7H-indolo[3,2-b][1,5]benzoxazepine-6(5H)-one.

A solution of 1.5g of 3-[o-aminophenoxy]-indole-2-carboxylic acid in 50ml of THF was treated with 1.48g of EEDQ and the clear solution left 18 hours at ambient temperature. The THF was removed by distillation, and the residue was rubbed with 2N HCl to give a yellow solid. Recrystallization from ethanol gave analytical material, mp. 233°–234°.

Anal. Calcd. for $C_{15}H_{10}N_2O_2$: C, 71.97; H, 4.03; N, 11.20. Found: C, 71.96; H, 4.02; N, 11.21.

EXAMPLE 5

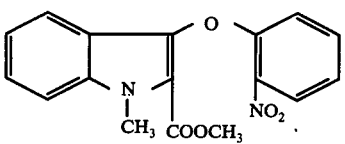

Methyl-3-[o-nitrophenoxy]-1-methyl-indole-2-carboxylate.

6.73g (0.16 mole) of 57% sodium hydride in mineral oil was washed with hexane and suspended in 500ml of THF. To this was added 43.4g (0.139 mole) of methyl-3-[o-nitrophenoxy]-indole-2-carboxylate. The mixture was stirred at reflux for 1 hour, then 42.6g (0.3 mole) of methyl iodide was added and reflux continued for 3 hours. Water (5ml) was added, the THF removed by distillation and the gummy residue recrystallized from isopropanol to give analytical material as yellow needles, mp. 119°–121°.

Anal. Calcd. for $C_{17}H_{14}N_2O_5$: C, 62.57; H, 4.32; N, 8.59. Found: C, 62.68; H, 4.38; N, 8.72.

EXAMPLE 6

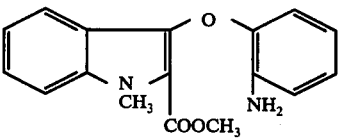

Methyl-3[o-aminophenoxy]-1-methyl-indole-2-carboxylate.

In the same way as described in example 2, methyl-3-[o-nitrophenoxy]-1-methyl indole-2-carboxylate was reduced and the crude product recrystallized from methanol to give analytical material, mp. 103°–105°.

Anal. Calcd. for $C_{17}H_{16}N_2O_3$: C, 68.90; H, 5.44; N, 9.45. Found: C, 68.75; H, 5.60; N, 9.58.

EXAMPLE 7

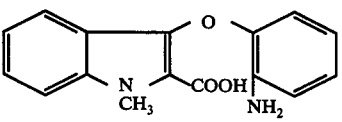

3-[o-aminophenoxy]-1-methyl-indole-2-carboxylic acid.

In the same way as described in example 3, methyl-3-[o-aminophenoxy]-1-methyl-indole-2-carboxylate was hydrolyzed and the crude product recrystallized from ethanol to give analytical material, mp. 193°–194°.

Anal. Calcd. for $C_{16}H_{14}N_2O_3$: C, 68.07; H, 5.00; N, 9.92. Found: C, 67.94; H, 5.22; N, 9.97.

EXAMPLE 8

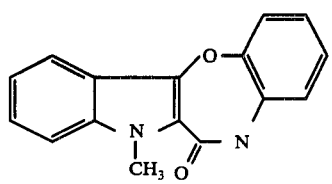

7-methyl-7H-indolo[3,2-b][1,5]benzoxazepine-6(5H)-one.

In the same way as described in example 4, 3-[o-aminophenoxy]-1-methyl-indole-2-carboxylic acid was cyclized with EEDQ. Analytical material was obtained by recrystallization from acetonitrile, mp. 247°-248°.

Anal. Calcd. for $C_{16}H_{12}N_2O_2$: C, 72.71; H, 4.58; N, 10.60. Found: C, 72.69; H, 4.66; N, 10.85.

EXAMPLE 9

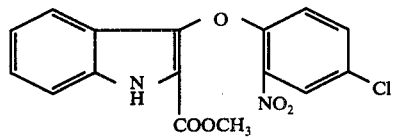

Methyl-3-[2-nitro-4-chlorophenoxy]-indole-2-carboxylate.

In the same way as described in example 1, methylindoxylate and 2,5-dichloronitrobenzene were reacted. Recrystallization from ethanol gave analytical material, mp. 171°-172°.

Anal. Calcd. for $C_{16}H_{11}N_2O_5Cl$: C, 55.43; H, 3.20; N, 8.08; Cl, 10.72. Found: C, 55.24; H, 3.48; N, 7.88; Cl, 10.50.

EXAMPLE 10

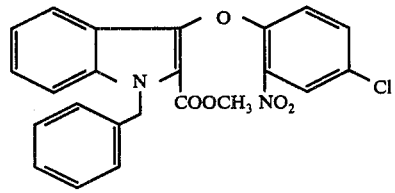

Methyl-3-[2-nitro-4-chlorophenoxy]-1-benzyl-indole-2-carboxylate.

In the same way as described in example 5, methyl-3-[2-nitro-4-chlorophenoxy]-indole-2-carboxylate was alkylated with benzyl bromide. Analytical material was obtained by recrystallization from ethanol, mp. 120°-121°.

Anal. Calcd. for $C_{23}H_{17}N_2O_5Cl$: C, 63.24; H, 3.92; N, 6.41; Cl, 8.12. Found: C, 63.15; H, 3.97; N, 6.39; Cl, 8.30.

EXAMPLE 11

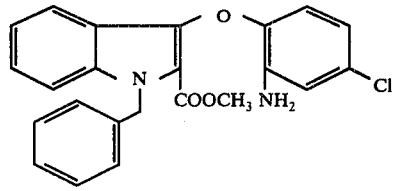

Methyl-3-[2-amino-4-chlorophenoxy]-1-benzyl-indole-2carboxylate.

In the same way as described in example 2, methyl-3-[2-nitro-4-chlorophenoxy]-1-benzyl-indole-2-carboxylate was reduced and the crude product recrystallized from ethanol to give analytical material, mp. 121°-123°.

Anal. Calcd. for $C_{23}H_{19}N_2O_3Cl$: C, 67.90; H, 4.71; N, 6.88; Cl 8.71. Found: C, 67.85; H, 4.80; N, 6.76; Cl, 8.96.

EXAMPLE 12

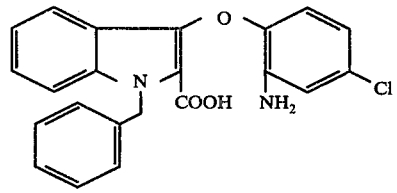

3-[2-amino-4-chlorophenoxy]-1-benzyl-indole-2-carboxylic acid.

In the same way as described in example 3, methyl-3-[2-amino-4-chlorophenoxy]-1-benzyl-indole-2-carboxylate was hydrolyzed and the crude product recrystallized from 95% ethanol to give analytical material, mp. 218°-219°.

Anal. Calcd. for $C_{22}H_{17}N_2O_3Cl$: C, 67.26; H, 4.36; N, 7.13; Cl, 9.02. Found: C, 67.17; H, 4.40; N, 7.05; Cl, 9.19.

EXAMPLE 13

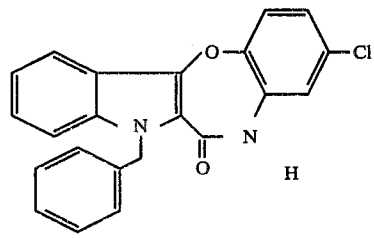

3-chloro-7-benzyl-7H-indolo[3,2-b][1,5]benzoxazepine-6(5H)-one.

In the same way as described in example 4, 3-[2-amino-4-chlorophenoxy]-1-benzyl-indole-2-carboxylic acid was cyclized, and the crude product was recrystallized from aqueous THF to give analytical material, mp. 259°-261°.

Anal. Calcd. for $C_{22}H_{15}N_2O_2Cl$: C, 70.50; H, 4.03; N, 7.47; Cl, 9.46. Found: C, 70.48; H, 4.12; N, 7.20; Cl, 9.59.

EXAMPLE 14

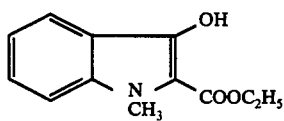

Ethyl-N-methyl indoxylate.

A mixture of 38.8g (0.2 mole) of ethyl chloromalonate and 44g (0.41 mole) of N-methylaniline was heated on the steam bath for 72 hours. After cooling, the mixture was diluted with 500ml of methylene chloride and unreacted N-methylaniline extracted with 4N HCl. The methylene chloride layer was dried and concentrated to 49g of oil. This was diluted with 49ml of hexamethylphosphoramide, and the mixture was heated rapidly to boiling (bath temp. 245°). Reflux was continued for 20 minutes, the mixture cooled rapidly and poured into 400ml of 4N HCl. The crude solid product was filtered and recrystallized from isopropanol to give crystals, mp. 95°–96°.

EXAMPLE 15

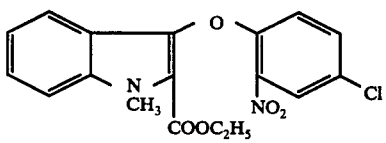

Ethyl-3-[2-nitro-4-chlorophenoxy]-1-methyl-indole-2-carboxylate.

In the same way as described in example 1, ethyl-N-methyl indoxylate was alkylated with 2,5-dichloro nitrobenzene and the crude product recrystallized from isopropanol to give analytical material, mp. 133°–134°.

Anal. Calcd. for $C_{18}H_{15}N_2O_5Cl$: C, 57.69; H, 4.03; N, 7.47; Cl, 9.46. Found: C, 57.97; H, 4.09; N, 7.47; Cl, 9.70.

EXAMPLE 16

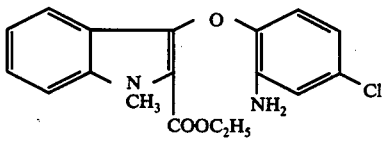

Ethyl-3-[2-amino-4-chlorophenoxy]-1-methyl-indole-2-carboxylate.

In the same way as described in example 2, ethyl-3-[2-nitro-4-chlorophenoxy]-1-methyl-indole-2-carboxylate was reduced and the crude product recrystallized from ethanol, mp. 118°–120°.

Anal. Calcd. for $C_{18}H_{17}N_2O_3Cl$: C, 62.70; H, 4.97; N, 8.12; Cl, 10.28. Found: C, 62.82; H, 5.07; N, 8.05; Cl, 10.56.

EXAMPLE 17

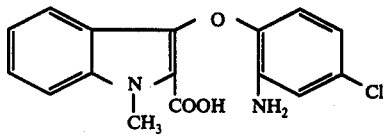

3-[2-amino-4-chlorophenoxy]-1-methyl-indole-2-carboxylic acid.

In the same way as described in example 3, ethyl-3-[2-amino-4-chlorophenoxy]-1-methyl-indole-2-carboxylate was hydrolyzed and the crude product recrystallized from 95% ethanol to give analytical material, mp. 204°–206°.

Anal. Calcd. for $C_{16}H_{13}N_2O_3Cl$: C, 60.67; H, 4.14; N, 8.84; Cl, 11.19. Found: C, 60.70; H, 4.21; N, 8.90; Cl, 11.09.

EXAMPLE 18

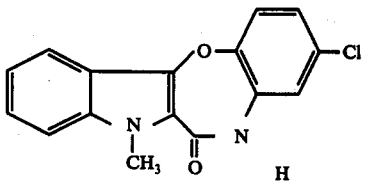

3-chloro-7-methyl-7H-indolo[3,2-b][1,5]benzoxazepine-6(5H)-one.

In the same way as described in example 4, 3-[2-amino-4-chlorophenoxy]-1-methyl-indole-2-carboxylic acid was cyclized, and the crude product, insoluble in all solvents, was purified by digesting for 1 hour in hot THF and filtering while hot, mp. 306°–307°.

Anal. Calcd. for $C_{16}H_{11}N_2O_2Cl$: C, 64.33; H, 3.71; N, 9.38; Cl, 11.87. Found: C, 64.20; H, 3.73; N, 9.15; Cl, 12.40.

EXAMPLE 19

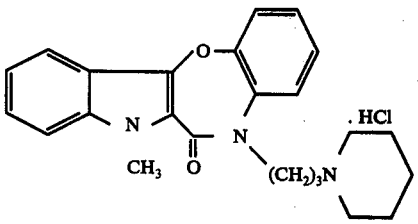

7-methyl-5-(3-piperidinopropyl)-7H-indolo[3,2b][1,5]benzoxazepin-6(5H)-one hydrochloride.

A mixture of 1.8g of 7methyl-7H-indolo [3,2-b][1,5]benzoxazepin-6(5H)-one, 0.42g of 57% sodium hydride-mineral oil dispersion and 10ml of THF was refluxed for 15 min. and then treated with 4.0 g of 3-chloropropylpiperidine. The mixture was refluxed for 24 hrs., diluted with 2N HCl and extracted with ether. The aqueous layer was made basic with 5% NaOH and the oil extracted with ether. The ether phase was dried and treated with dry HCl to give a white solid. The solid was recrystallized from methanol-ether to give analytical material, mp. 205°–206°.

Anal. Calcd. for $C_{24}H_{27}N_3O_2 \cdot HCl$: C, 67.67; H, 6.63; N, 9.86; Cl, 8.32. Found: C, 67.56; H, 6.78; N, 9.72; Cl, 8.59.

EXAMPLE 20

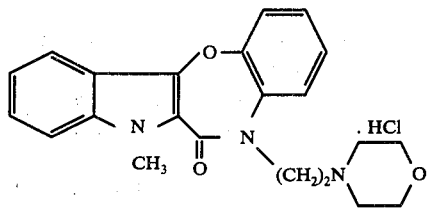

7-methyl-5-(3-morpholinoethyl)-7H-indolo[3,2b][1,5-]benzoxazepine-6(5H)-one hydrochloride.

In the same way as described in example 19, 7-methyl-7H-indolo[3,2b][1,5]benzoxazepine-6(5H)-one was alkylated with 2-(chloroethyl)morpholine and the crude hydrochloride recrystallized from ethanol to give analytical material, mp. 266°–268°.

Anal. Calcd. for $C_{22}H_{23}N_3O_3HCl$; C, 63.84; H, 5.84; N, 10.15; Cl, 8.57. Found: C, 63.58; H, 5.86; N, 10.25; Cl, 8.49.

EXAMPLE 21

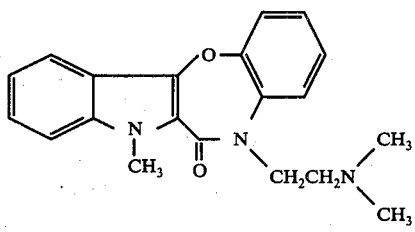

7-methyl-5-[(2-dimethylamino)ethyl]-7H-indolo-[3,2-b][1,5]benzoxazepine-6(5H)-one.

In the same way as described in example 19, 7-methyl-7H-indolo[3,2-b][1,5]benzoxazepine-6(5H)-one was alkylated with dimethylaminoethyl chloride, and the crude base obtained by removal of the ether was recrystallized from methanol, mp. 119°–121°.

Anal. Calcd. for $C_{20}H_{21}N_3O_2$: C, 71.62; H, 6.31; N, 12.53. Found: C, 71.66; H, 6.40; N, 12.69.

EXAMPLE 22

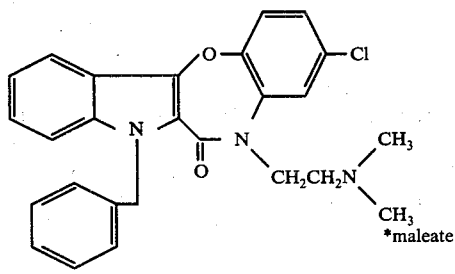

7-benzyl-3-chloro-5[2-(dimethylamino)ethyl]-7H-indolo[3,2-b][1,5]benzoxazepine-6(5H)-one maleate.

In the same way as described in example 19, 3-chloro-7-benzyl-7H-indolo[3,2-b][1,5]benzoxazepine-6-(5H)-one was alkylated with dimethylaminoethyl chloride. The crude-free base gave a crystalline salt on treatment with maleic acid in ethanol. Recrystallization from isopropanol gave analytical material, mp. 168°–170°.

Anal. Calcd. for $C_{26}H_{24}N_3O_2Cl \cdot C_4H_4O_4$: C, 64.11; H, 5.02; N, 7.48; Cl, 6.31. Found: C, 63.98; H, 5.06; N, 7.34; Cl, 6.60.

EXAMPLE 23

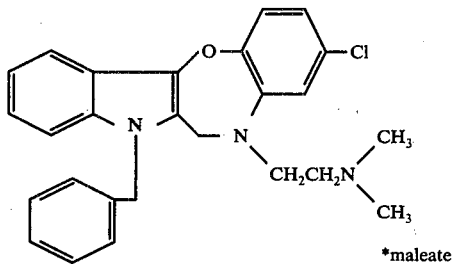

7-benzyl-3-chloro-5-[(2-dimethylamino)ethyl]-6,7-dihydro-5H-indolo[3,2-b][1,5]benzoxazepine maleate.

A solution of 7.8g of 7-benzyl-3-chloro-5[(2-dimethylamino)ethyl]-7H-indolo[3,2-b][1,5]benzoxazepine-6(5H)-one in 100 ml of ether was added dropwise to a suspension of 0.76g of lithium aluminum hydride in ether. The mixture was stirred for 18 hours at ambient temperature, decomposed with saturated NH$_4$Cl solution, and the alumina filtered and washed with ether. The ether solution was concentrated to a gum; the gum taken up in ethanol and treated with 2.0g of maleic acid. The crude salt was recrystallized from ethanol for analysis, mp. 149°–151°.

Anal. Calcd. for $C_{26}H_{26}N_3OCl \cdot C_4H_4O_4$: C, 65.75; H, 5.52; N, 7.67; Cl, 6.47. Found: C, 64.10; H, 5.73; N, 7.20; Cl, 6.44.

EXAMPLE 24

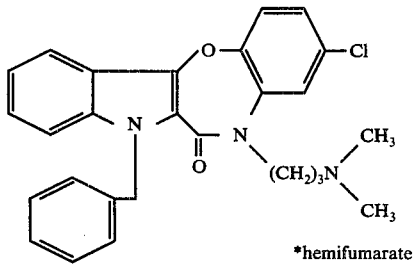

7-benzyl-3-chloro-5-[(3-dimethylamino)propyl]-7H-indolo-[3,2-b][1,5]benzoxazepine-6(5H)-one hemifumarate.

In the same way as described in example 19, 3-chloro-7-benzyl-7H-indolo[3,2-b][1,5]-benzoxazepine-6(5H)-one was alkylated with 3-dimethylaminopropyl chloride. The crude base was treated with fumaric acid in ethanol and the salt recrystallized from methanol, mp. 203°-205°.

Anal. Calcd. for $C_{27}H_{26}N_3O_2Cl \cdot \frac{1}{2}C_4H_4O_4$: C, 67.24; H, 5.45; N, 8.11; Cl, 6.84. Found: C, 67.25; H, 5.51; N, 7.93; Cl, 6.41.

EXAMPLE 25

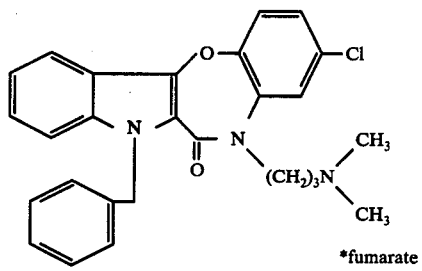

*fumarate 7-benzyl-3-chloro-5-[3-(dimethylamino)propyl]-6,7-dihydro-5H-indolo[3,2-b][1,5benzoxazepine fuamarate.

In the same way as described in example 23, 7-benzyl-3-chloro-5-[(3-dimethylamino)propyl]-7H-indolo-[3,2-b][1,5]benzoxazepine-6(5H)-one was reduced. The crude base in ethanol was treated with fumaric acid and the salt recrystallized from ethanol, mp. 146°-147°.

Anal. Calcd. for $C_{27}H_{28}N_3Ocl \cdot C_4H_4O_4$: C, 66.25; H, 5.74; N, 7.48; Cl, 6.31. Found: C, 66.45; H, 5.84; N, 7.33; Cl, 6.39.

EXAMPLE 26

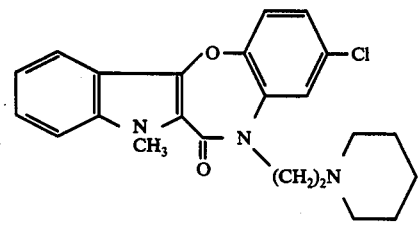

3-chloro-7-methyl-5-(2-piperidinoethyl)-7H-indolo-[3,2-b][1,5]benzoxazepine-6(5H)-one.

In the same way as described in example 19, 3-chloro-7-methyl-7H-indolo[3,2-b][1,5]benzoxazepin-6(5H)-one was alkylated with piperidinoethyl chloride. The crude solid base was recrystallized from acetonitrile, mp. 160°-162°.

Anal. Calcd. for $C_{23}H_{24}N_3O_2Cl$: C, 67.39; H, 5.90; N, 10.25; Cl, 8.65. Found: C, 67.34; H, 5.94; N, 10.10; Cl, 8.56.

EXAMPLE 27

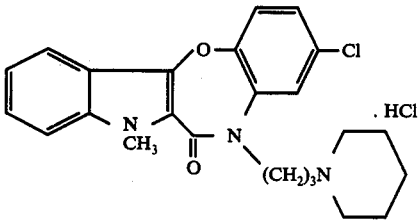

3-chloro-7-methyl-5-(3-piperidinopropyl)-7H-indolo-[3,2-b][1,5]benzoxazepin-5(5H)-one hydrochloride.

In the same way as described in example 19, 3-chloro-7-methyl-7H-indolo-[3,2-b][1,5]benzoxazepin-6(5H)-one was alkylated with 3-chloropropyl piperidine, and the crude salt was recrystallized from isopropanol, mp. 202°-204°.

Anal. Calcd. for $C_{24}H_{26}N_3O_2Cl \cdot HCl$ C, 62.61; H, 5.91; N, 9.13; Cl, 15.40. Found: C, 62.31; H, 5.98; N, 9.12; Cl, 15.37.

As stated earlier, the compounds of this invention are suitably and generally administered in oral dosage form, such as by tablet or capsule, by combining the same in an effective amount with any oral pharmaceutically acceptable inert diluent, such as lactose, starch, dicalcium phosphate, calcium sulfate, kaolin, mannitol and powdered sugar. In addition, when required, suitable binders, lubricants, disintegrating agents, and coloring agents can also be added. Typical binders include starch, gelatin, sugars such as sucrose, molasses, and lactose, natural and synthetic gums such as acacia sodium alginate, extract of Irish moss, carboxymethyl cellulose, methyl cellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methyl cellulose, agar, bentonite, cellulose and wood products, alginic acid, guar gum, citris pulp, carboxymethyl cellulose, and sodium lauryl sulfate. If desired, conventionally pharmaceutically acceptable dyes such as any of the standard FD & C dyes may be incorporated into the dosage unit form.

From the foregoing description, one skilled in the art can easily ascertain the essential characteristics of this invention and without departing from the spirit and scope thereof can make various changes and/or modifications to the invention for adapting it to various usages and conditions. Accordingly, such changes and modifications are probably intended to be within the full range of equivalents of the following claims.

I claim:

1. A method of producing a central nervous system depressant activity in a mammal which comprises the administration of an effective CNS depressing amount of a compound or a pharmaceutical composition comprising a compound of the general formula:

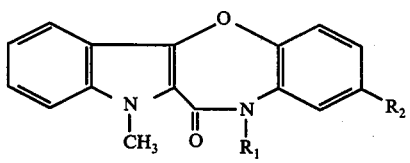

wherein $R_1$ is selected from the group consisting of

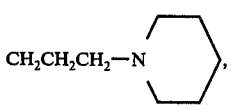

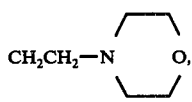

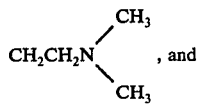

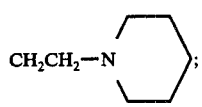

wherein $R_2$ is selected from the group consisting of

—Cl, and

—H;

or the pharmaceutically acceptable salts thereof to said mammal.

2. A method according to claim 1 wherein $R_1$ of the compound is

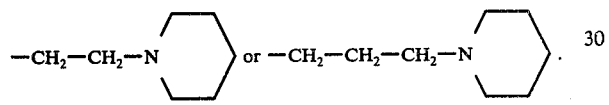

3. The method according to claim 2 wherein the compound is 7-methyl-5-(3-piperidinopropyl)-7H-indolo[3,2-b]-[1,5]benzoxazepin-6(5H)-one.

4. The method according to claim 2 wherein the compound is 3-chloro-7-methyl-5-[2-(1-piperidinyl)ethyl]-7H-indolo-[3,2-b][1,5]benzoxazepin-6(5H)-one.

5. The method according to claim 2 wherein the compound is 3-chloro-7-methyl-5-[3-(1-piperidinyl)propyl]-7H-indolo-[3,2-b][1,5]benzoxazepin-6(5H)-one.

6. The method according to claim 1 wherein the compound is 5-[2-(dimethylamino)ethyl]-7-methyl-7H-indolo-[3,2-b][1,5]dibenzoxazepin-6(5H)-one.

7. The method according to claim 1 wherein the compound is 7-methyl-5-[2-(4-morpholinyl)ethyl]-7H-indolo[3,2-b][1,5]benzoxazepin-6(5H)-one.

8. A method of producing a central nervous system depressant activity in a mammal which comprises the administration to said mammal of an effective CNS depressing amount of a compound or a pharmaceutical composition comprising a compound of the formula:

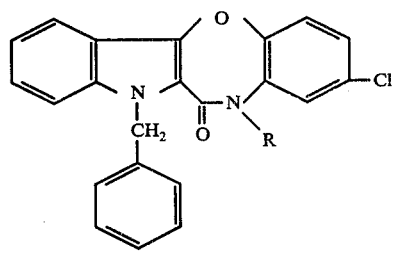

wherein R is

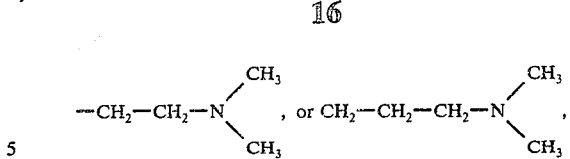

or the pharmaceutically acceptable salts thereof.

9. The method according to claim 8 wherein the compound is 3-chloro-5-[2-(dimethylamino)ethyl]-7-(phenylmethyl)-7H-indolo[3,2-b][1,5]benzoxazepin-6(5H)-one.

10. The method according to claim 8 wherein the compound is 3-chloro-5-[3-(dimethylamino)propyl]-7-(phenylmethyl)-7H-indolo[3,2-b][1,5]benzoxazepin-6-(5H)-one.

11. A method of producing a central nervous system depressant activity in a mammal which comprises the administration to said mammal of an effective CNS depressing amount of a compound or a pharmaceutical composition comprising a compound of the formula:

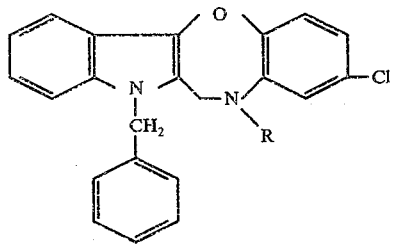

wherein R is

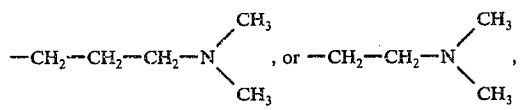

or the pharmaceutically acceptable salts thereof.

12. The method according to claim 11 wherein the compound is 3-chloro-6,7-dihydro-N,N-dimethyl-7-(phenylmethyl)-5H-indolo[3,2-b][1,5]benzoxazepine-5-propanamine.

13. The method according to claim 11 wherein the compound is 3-chloro-5-[2-(dimethylamino)ethyl]-6,7-dihydro-7-(phenylmethyl)-5H-indolo[3,2-b][1,5]benzoxazepine.

14. A method of producing a central nervous system depressant activity in a mammal which comprises the administration to said mammal of an effective CNS depressing amount of a compound or a pharmaceutical composition comprising a compound of the formula:

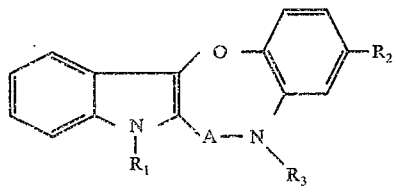

wherein $R_1$ is hydrogen, lower alkyl of 1 to 6 carbon atoms or an aralkyl group of 1 to 6 carbon atoms in the chain; $R_2$ is hydrogen, a halogen atom such as fluorine or chlorine, lower alkyl of 1 to 6 carbon atoms or a trifluoromethyl group; A is a methylene group or a carbonyl group; $R_3$ is hydrogen, lower alkyl of 1 to 6 carbon atoms, an aralkyl group of 1 to 6 carbon atoms in the chain, or an ω-aminoalkyl group of the formula

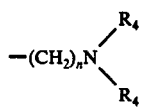

in which $n$ may be 2 to 4 and $R_4$ is hydrogen, lower alkyl of 1 to 6 carbon atoms or, taken together with the N atom form a heterocyclic ring of the formula

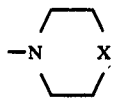

wherein X is oxygen, sulfur, —$CH_2CH_2$—, a bond connecting the adjacent carbon atoms, or CH—$R_5$ or N—$R_5$ wherein $R_5$ is hydrogen or lower alkyl of 1 to 6 carbon atoms, or the pharmaceutically acceptable salts thereof.

* * * * *